(12) United States Patent
Falloon et al.

(10) Patent No.: US 8,513,346 B2
(45) Date of Patent: Aug. 20, 2013

(54) FLAME RETARDANT COMPOSITION FOR USE IN STYRENICS

(75) Inventors: Stephen B. Falloon, Lafayette, IN (US); David W. Bartley, West Lafayette, IN (US); Julia E. Holland, Indianapolis, IN (US); Wayne Meyer, West Lafayette, IN (US); Steven Bakeis, West Lafayette, IN (US)

(73) Assignee: Chemtura Corporation, Middlebury, CT (US)

( * ) Notice: Subject to any disclaimer, the term of this patent is extended or adjusted under 35 U.S.C. 154(b) by 0 days.

(21) Appl. No.: 13/421,983

(22) Filed: Mar. 16, 2012

(65) Prior Publication Data

US 2012/0184638 A1    Jul. 19, 2012

Related U.S. Application Data

(62) Division of application No. 12/009,052, filed on Jan. 15, 2008, now abandoned.

(60) Provisional application No. 60/905,328, filed on Mar. 7, 2007.

(51) Int. Cl.
*C08K 5/03* (2006.01)
*C07C 17/12* (2006.01)
*C07C 17/14* (2006.01)

(52) U.S. Cl.
CPC . *C08K 5/03* (2013.01); *C07C 17/12* (2013.01); *C07C 17/14* (2013.01)
USPC .......... 524/464; 570/182; 570/183; 570/184; 570/185

(58) Field of Classification Search
CPC .......... C07C 17/12; C07C 17/14; C08K 5/03
USPC ................ 570/182–185; 524/464
See application file for complete search history.

(56) References Cited

U.S. PATENT DOCUMENTS 3,883,481 A * 5/1975 Kopetz et al. ................ 524/288
2008/0281024 A1 * 11/2008 Oren et al. .................... 524/151

* cited by examiner

*Primary Examiner* — Ling Choi
*Assistant Examiner* — Brieann R Fink
(74) *Attorney, Agent, or Firm* — Joseph Suhadolnik; Chemtura Corporation; George Romanik

(57) ABSTRACT

A method for flame-retarding styrenic resins is disclosed wherein the method comprises incorporating in compositions an effective amount of at least one flame retardant compound comprising both aliphatic and aromatic bromine.

8 Claims, No Drawings

FLAME RETARDANT COMPOSITION FOR USE IN STYRENICS

This patent application is a divisional of U.S. patent application Ser. No. 12/009,052, filed Jan. 15, 2008 now abandoned, which application claims benefit under 35 USC 119(e) of U.S. Provisional Application No. 60/905,328, filed Mar. 7, 2007, the disclosures of each are incorporated herein by reference.

BACKGROUND OF THE INVENTION

1. Field of the Invention

The present invention is related to flame retardants. More particularly, the present invention is related to flame retardants comprising both aliphatic and aromatic bromine for use with styrenic resins.

2. Description of Related Art

Styrenic resins are well known in the synthetic organic polymer art as a class of thermoplastics that offer excellent mechanical properties as well as good chemical resistance. The properties that make styrenics useful for many applications as solid polymers also make them very desirable as foamed polymers. A number of processes have been developed over the last forty years to prepare styrenic foams for a variety of applications, some of which require the use of flame retardants.

A flame retardant, such as a halogenated organic compound, is often incorporated into a formulated resin in order to render the resin resistant to ignition. It is known that brominated aliphatic compounds, brominated aromatic compounds, and mixtures thereof have been used in solid and foamed styrenic applications. Hexabromocyclododecane (HBCD) is one such known aliphatic brominated flame retardant that has been used in foamed styrenic applications. HBCD is a highly brominated aliphatic flame retardant that has unusually high thermal stability, which results in excellent performance at low loading levels with a minimum effect on polymer properties.

Recently there have been concerns about the health and environmental impact of some flame retardants including HBCD. Although scientific studies have not necessarily shown significant risks to human health or the environment, there are ongoing reviews by various regulatory agencies that may result in reduced usage of HBCD. In the event that these agencies limit the usage of HBCD, extruded polystyrene foam and expanded polystyrene foam manufacturers may be required to choose an alternative flame retardant, and many may adopt a substitute before any regulatory mandate. Thus, there exists a need for a flame retardant alternative to HBCD that is more environmentally friendly and maintains all of the performance properties of HBCD.

WO 2007/057900 discloses polybrominated bisaryl compounds containing bromomethyl or bromomethylene groups, as well as flameproof polymeric formulations comprising the compounds. These compounds are said to exhibit good thermal stability and to be particularly suitable for flame-retarding polystyrene thermoplastic foams. A process for making the polybrominated bisaryl compounds is also disclosed.

WO 2006/008738 discloses a process for the preparation of highly pure pentabromobenzyl bromide, wherein the benzylic bromination reaction is carried out in a suitable organic solvent in the presence of water and wherein the reaction temperature is such that it is sufficient to activate the initiator but not high enough to consume a substantial amount thereof.

WO 2006/013554 discloses a styrenic polymer composition comprising a flame-retardant effective amount of a compound of formula (I): $(C_6H_{(5-n)}Y_n)CH_2X$, wherein X is Cl or Br; Y is Cl or Br; and n is an integer between 1 and 5; or a mixture of two or more of said compounds of formula (I) or their homologues and derivatives or other Br—FRs.

GB 1,107,283 discloses a granular expandable polystyrene composition that contains as a fire-retardant a minor amount of a compound of formula $Ar(Br)_m(Cl)_nR$ or $Ar(Br)_x(Cl)_yOR$ where Ar is an aryl residue, m is 1-4, n is 0-2, x is 1 or more, y is 0 or an integer and R is hydrogen, a straight or branched chain alkyl group which may be halogenated, a straight or branched chain alkenyl group or a halogenated aryl group; there being at least 2 nuclear bromine atoms per molecule of the above compound. The compound may be tetrabromobenzene, tribromophenol, pentabromophenyl (allyl, ethyl or n-propyl)ether, an isomer of tribromotoluene or tribromophenyl allyl ether, chlorodibromotoluene, chlorodibromophenyl allyl ether, hexabromodiphenyl ether, dibromodiphenyl, dibromonaphthalene; 2,4-dibromo-1-methylnaphthalene; 1,5-dibromoanthracene; pentabromophenyl dibromopropyl ether, pentabromophenol or tetrabromochlorophenol. The composition may also contain dicumyl or di-tert. butyl peroxide, tert. butyl peracetate or cumene hydroperoxide. The compositions may be made by polymerizing styrene in the presence of the fire-retardant compound, polystyrene granules, benzoyl peroxide, water and petroleum ether as expanding agent and the resulting polymer may be granulated, expanded by heating in steam and then moulded into a block.

GB 1,394,787 discloses a flame resistant polystyrene or styrene-containing copolymer containing hexabromoxylene. There is further disclosed a self-extinguishing mouldable composition or moulding comprising polystyrene or a styrene-containing copolymers and hexabromoxylene in an amount of from 0.5 to 8.0 percent by weight, based on the total weight of the mould able composition or moulding.

EP 0502333 discloses a process for preparing a mixture of brominated, non-condensed ring polyaromatics, which process comprises brominating the precursor non-condensed ring polyaromatic in the presence of a bromination catalyst. The mixture has an average bromine number of 5.8 to 6.2, more than about 55 GC area percent of the hexabromo homolog, and a reduced amount of light-end impurities.

U.S. Pat. No. 4,024,092 discloses polymer compositions having enhanced oxygen index values as measured by ASTM Method D-2863-70, which compositions contain effective amounts of a bromo or chloro derivative of stilbene.

U.S. Pat. No. 5,039,729 discloses mixtures of brominated diphenyl ethanes, such mixtures containing a predominant amount of hexabromodiphenyl ethane and having an average bromine number, based upon GC area percent, of from about 6.7 to about 7.3. ABS based formulations containing such mixtures and articles made from such formulations are also disclosed.

U.S. Pat. No. 5,055,235 discloses a process for preparing a mixture of brominated, non-condensed ring polyaromatics, which process features multiple bromination temperatures and multiple catalyst additions for brominating the precursor non-condensed ring polyaromatic. The mixture has an average bromine number of about 6 to about 8 bromine atoms per molecule, a low melting point range, and a low amount of light end impurities.

U.S. Pat. Nos. 5,741,949 and 6,117,371 disclose a process for producing a brominated, non-fused aromatic composition that involves a continuous bromination in a continuous, mixed reactor such as a continuous stirred tank reactor. Bromine and the aromatic substrate, and optionally a bromination catalyst, are continuously fed to a reaction zone to form a reaction mixture, and the reaction mixture is continuously withdrawn from the reaction zone after an established average residence time. Bromination levels can be readily controlled by controlling the average residence time of the reaction mixture within the reaction zone. Preferred continuous processes also provide mixed, brominated compositions having product distributions which are substantially broader than that obtained by batch brominations conducted to achieve the same level of bromination. Preferred products thus have broad melting ranges which are advantageous in compounding operations.

U.S. Pat. No. 5,821,393 discloses a process for the preparation of an aromatic bromoalkyl-substituted hydrocarbon compound, in which an alkyl-substituted aromatic hydrocarbon compound is reacted with a brominating agent in the presence of water.

U.S. Pat. No. 6,743,825 discloses an additive mixture said to be useful as a flame retardant. The mixture is comprised of (i) a poly(bromophenyl)alkane having in the molecule in the range of 13 to 60 carbon atoms and in the range of two to four aryl groups and (ii) a poly(bromophenyl)bromoalkane having in the molecule in the range of 13 to 60 carbon atoms and in the range of two to four aryl groups, said poly(bromophenyl)bromoalkane being in an amount which is greater than 25 wt %, based on the total weight of the additive mixture. A process for making the poly(bromophenyl)bromoalkane is also disclosed.

The disclosures of the foregoing are incorporated herein by reference in their entirety.

SUMMARY OF THE INVENTION

In evaluating alternatives for HBCD, it is important to maintain the good properties of high efficiency at low usage levels and high thermal stability. According to the present invention, it has been found that a single flame retardant compound containing both aliphatic and aromatic bromine can be used to flame retard styrenic resins, in particular, foamed styrenic resins. More surprisingly, the molecules containing aromatic bromine and benzylic bromine have been found to have the necessary thermal stability and to be most efficient when compared by lab scale flammability tests.

More particularly, the present invention is directed to a method for flame retarding styrenic resins comprising incorporating an effective amount of at least one flame retardant compound comprising both aliphatic and aromatic bromine.

In another aspect, the present invention is directed to an article of manufacture comprising a styrenic resin composition or foamed styrenic resin composition wherein said composition comprises an effective amount of at least one flame retardant compound comprising both aliphatic and aromatic bromine. In a preferred embodiment, in the article the flame retardant compound has an LOI of greater than 24 @ 5 phr when formulated into the resin in the range of 2-10 phr and a 5% weight loss based on TGA analysis of above 200.degree. C.

DESCRIPTION OF THE PREFERRED EMBODIMENT(S)

As noted above, the present invention relates to the use of compounds comprising both aliphatic and aromatic bromine to flame retard styrenic resins.

Examples of target molecules within the scope of the present invention are shown below:

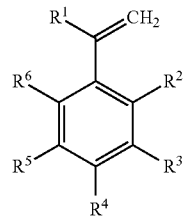

wherein $R^1$, $R^2$, $R^3$, $R^5$, and $R^6$ are independently selected from the group consisting of hydrogen and bromine, and $R^4$ is selected from the group consisting of hydrogen, bromine, and $CH_2Br$;

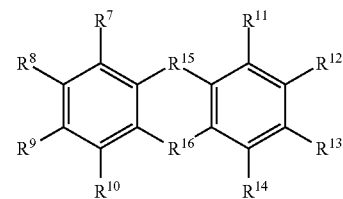

wherein $R^7$ through $R^{14}$ are independently selected from the group consisting of hydrogen and bromine, $R^{15}$ is selected from the group consisting of $CH_m$.sub.2 and CHBr, and $R^{16}$ is selected from the group consisting of $CH_2$, CHBr, and a fused ring;

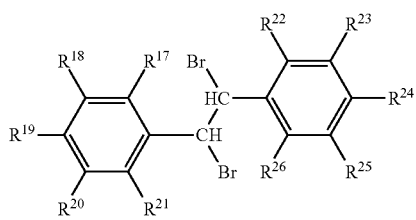

wherein $R^{17}$ through $R^{26}$ are independently selected from the group consisting of hydrogen and bromine, provided that no more than seven of $R^{17}$ through $R^{26}$ are bromine;

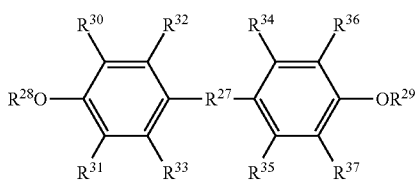

wherein $R^{27}$ is selected from the group consisting of alkyl, aryl, alkaryl, and $SO_2$, $R^{28}$ and $R^{29}$ are independently selected from the group consisting of hydrogen and alkyl, $R^{30}$, $R^{31}$, $R^{36}$, and $R^{37}$ are independently selected from the group consisting of methyl and $CH_2Br$, and $R^{32}$ through $R^{35}$ are independently selected from the group consisting of hydrogen and bromine;

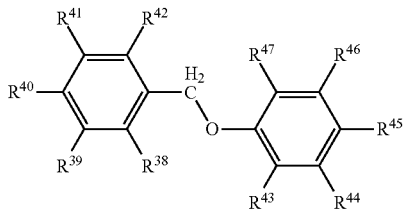

wherein $R^{38}$ through $^{42}$ are independently selected from the group consisting of hydrogen, bromine, $CH_2Br$, and alkyl, and $R^{43}$ through $R^{47}$ are independently selected from the group consisting of hydrogen and bromine; and

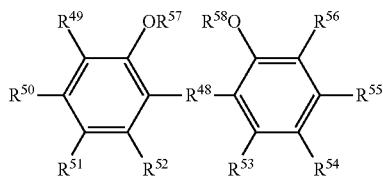

wherein $R^{48}$ is selected from the group consisting of alkyl, aryl, alkaryl, and $SO_2$, $R^{49}$ through $R^{52}$ are independently selected from the group consisting of $CH_3$ and $CH_2Br$, $R^{53}$ through $R^{56}$ are independently selected from the group consisting of hydrogen and bromine, and $R^{57}$ and $R^{58}$ are independently selected from the group consisting of hydrogen and alkyl; provided that in each of the foregoing structures, there is at least one aliphatic bromine and at least one aromatic bromine.

In the foregoing structural formulae, where an R group is:

a "fused ring", it is a fused ring of from 5 to 8 carbon atoms;

"alkyl", it is an alkyl group of from 1 to 6 carbon atoms;

"alkaryl", it is an alkaryl group comprising at least one alkyl group side chain of from 1 to 6 carbon atoms.

Examples of specific molecules that can be employed in the practice of the present invention include, but are not limited to, 1,1'-(1,2-dibromo-1,2-ethanediyl)bis-tribromobenzene, 1-bromoethyl dibromobenzene, 1-bromoethyl tribromobenzene, 1-bromoethyl tetrabromobenzene, bis-(1-bromoethyl) benzene, bis-(1-bromoethyl)bromobenzene, bis-(1-bromoethyl)dibromobenzene, bis-(1-bromoethyl)tribromobenzene, bis-(1-bromoethyl)tetrabromobenzene, 9,10-dibromo-9,10-dihydro octabromoanthracene, 9,10-dibromo-9,10-dihydro septabromoanthracene, 9,10-dibromo9,10-dihydro hexabromoanthracene, 9,10-dibromo-9,10-dihydro pentabromoanthracene, 4-bromomethyl tetrabromobenzyl 2,4,6-tribromophenyl ether, 4-bromomethyl benzyl 2,4,6-tribromophenyl ether, and the like.

The most preferred molecules, owing to their balance of efficiency and thermal stability, are 1,1'-(1,2-dibromo-1,2-ethanediyl)bis-tribromobenzene and 9,10-dibromo-9,10-dihydrooctabromo anthracene. The 1,1'-(1,2-dibromo-1,2-ethanediyl)bis-tribromobenzene is prepared in such a way that there are eight major components and several minor components that average to an aromatic bromine content of 5.5-6 bromine atoms and an average amount of 1.7-1.9 aliphatic bromine atoms.

The styrene resins employed in the practice of the present invention are styrenic polymers, such as polystyrene, poly-(p-methylstyrene), poly-(α-methylstyrene), copolymers of styrene or α-methylstyrene with dienes or acrylic derivatives, such as, for example, styrene/butadiene, styrene/acrylonitrile, styrene/alkyl methacrylate, styrene/maleic anhydride, styrene/butadiene/ethylacrylate/styrene/acrylonitrile/methylacrylate, mixtures of high impact strength from styrene copolymers and another polymer, such as, for example, from a polyacrylate, a diene polymer or an ethylene/propylene/diene terpolymer; and block copolymers of styrene, such as, for example, styrene/-butadiene/styrene, styrene/isoprene/styrene, styrene/ethylene/butylene/styrene or styrene/ethylene/propoylene styrene. Styrenic polymers may additionally or alternatively include graft copolymers of styrene or .alpha.-methylstyrene such as, for example, styrene on polybutadiene, styrene on polybutadiene-styrene or polybutadiene-acrylonitrile; styrene and acrylonitrile (or methacrylonitrile) on polybutadiene and copolymers thereof; styrene and maleic anhydride or maleimide on polybutadiene; sytrene, acrylonitrile, and maleic anhydride or maleimide on polybutadiene; styrene, acrylonitrile, and methyl methacrylate on polybutadiene, styrene and alkyl acrylates or methacrylates on polybutadiene, styrene and acrylonitrile on ethylene/-propylene/diene terpolymers, styrene and acrylonitrile on polyacrylates or polymethacrylates, styrene and acrylonitrile on acrylate/butadiene copolymers, and the like.

Additionally, the styrenic resins can be in the form of foamed resins. These foamed resins can be comprised of any of the aforementioned styrenic resins. Processes for making foamed resins are of two main classes: expanded polystyrene foams (EPS) and extruded polystyrene foams (XPS). The specific procedures for forming the foamed resins are well defined in the art.

The flame retardants of the invention can be conventionally incorporated into the styrenic materials in flame retardant amounts. The amount of these flame retardants necessary for flame retardancy will depend upon the particular brominated substrate employed and styrenic material involved, as well as other flame retardants that might be included. Those of ordinary skill in the art will be readily able to incorporate an amount of the flame retardant which is necessary to achieve the desired level of flame retardancy. As is well known, it is often preferred to incorporate a brominated flame retardant with another flame retardant material, such as an inorganic compound, e.g. ferric oxide, zinc oxide, zinc borate, a group V element oxide such as a bismuth, arsenic, phosphorus or an antimony oxide.

In addition, foamed resins generally require additional materials to achieve the desired properties of the foam. These can include catalysts for polymerization, blowing agents, emulsifiers, and stabilizers. The exact compositions and quantities of other additives are known to those skilled in the art.

When selecting target molecules for screening, molecules containing only aliphatic, only aromatic, and a mix of aliphatic and aromatic bromine were considered. Examples of molecules used in the screening evaluations are shown below:

Aliphatic Only:
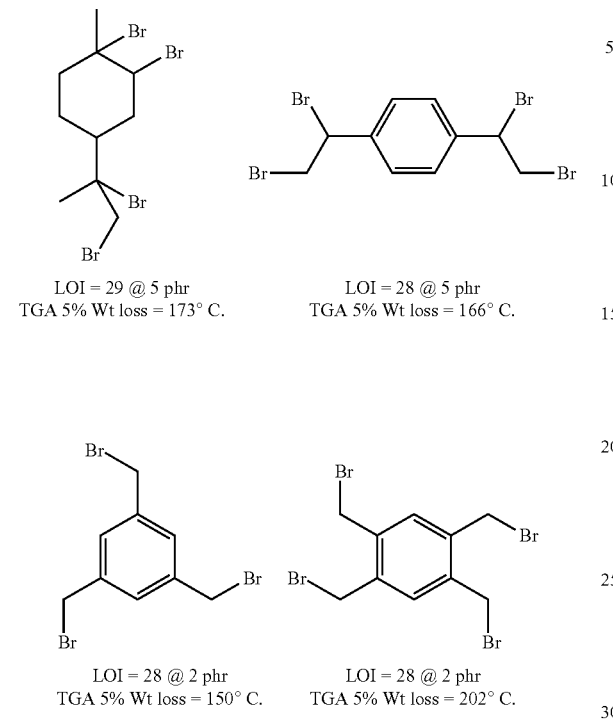
Aromatic Only:
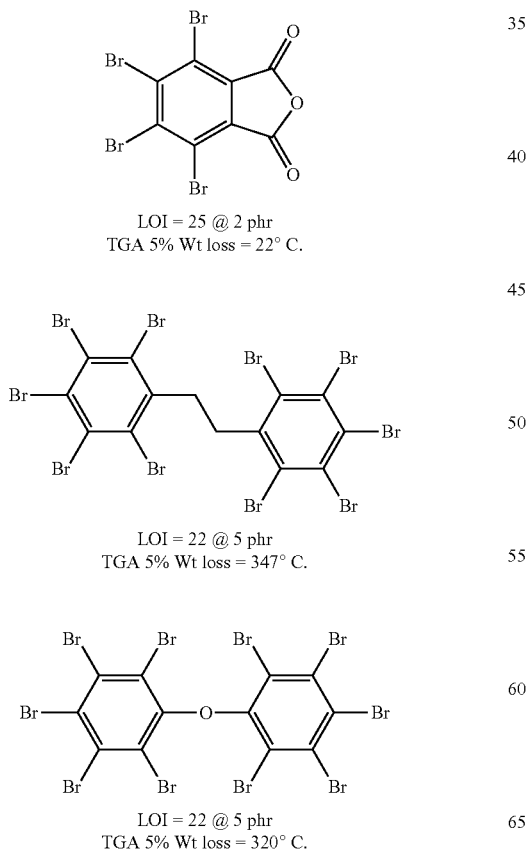
Aliphatic/Aromatic
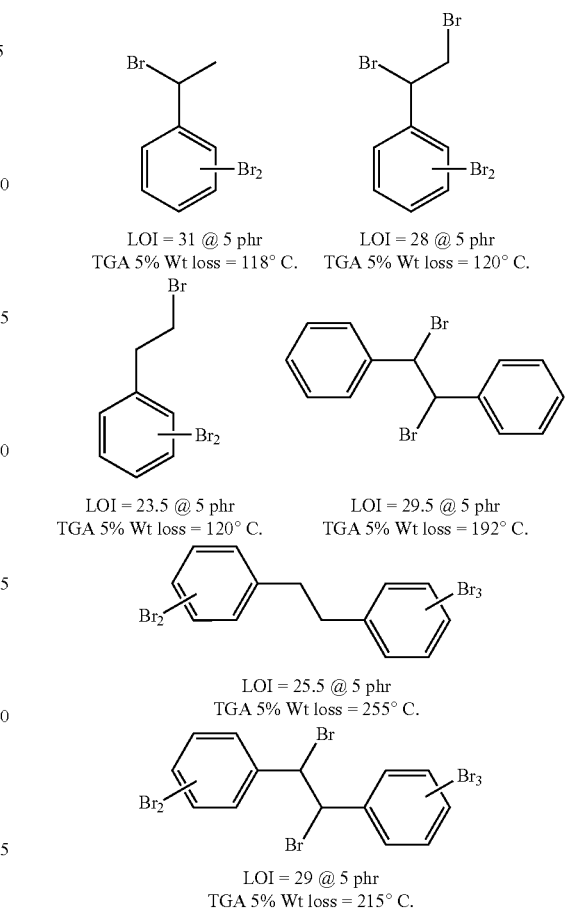
Polymeric Aliphatic/Aromatic
In the above, the values of m and n were not rigorously specified in the analytical data, but approximate numbers would be m=1 and n=1 in the first molecule and m=10 and n=1 in the second. This means that there is a higher amount of aliphatic (benzylic) bromine in the first molecule and a relatively low level of aliphatic (benzylic) bromine in the second molecule. The LOI data support the premise that one needs both aliphatic and aromatic bromine, and that benzylic bromine is even better.

In the above structures, the notation $Br_2$ is intended to mean two bromine atoms, each attached at separate points to the phenyl ring. Similarly, $Br_3$, $Br_x$, and $Br_y$ refer to 3 bromines, x bromines, and y bromines, respectively, where x and y are independently integers of from 1 to 3.

The target molecule must have an Limiting Oxygen Index (LOI) of more than 26 @ 5 phr and a 5% wt loss based on TGA analysis of more than 215° C. in order to be considered comparable to HBCD in end use EPS and XPS applications. When evaluating molecules that contain only aliphatic bromine, the molecules were determined to be efficient as demonstrated by the LOI performance shown above; however, the molecules did not meet the thermal criteria. Molecules containing only aromatic bromine were found to be more thermally stable; however, did not appear to have the necessary efficiency as determined by LOI.

Molecules containing both aliphatic and aromatic bromine were found to have the best balance of efficiency and thermal stability. It was surprisingly found that molecules containing aromatic bromine and benzylic bromine have the best balance of efficiency and thermal stability. This is demonstrated by the series of dibromostyrene molecules shown above where the LOI performance drops from 28-31 to 23 when the benzylic bromine is removed. This observation is also confirmed in the diphenylethane series shown above wherein, when the benzylic bromine is removed, the LOI drops from 29 to 25. This series of molecules also demonstrates the necessity for having aromatic bromine on the molecule in order to increase the thermal stability of the molecule.

EXAMPLES

Typical laboratory hand cast foams were prepared using the formulations listed below. Lab preparation yielded foams with comparable densities. The foams were then evaluated by ASTM D2863-00 and UL-94. ASTM D2863-00 is a test method used to determine the LOI, which is an indication of flame retardant effectiveness. Thermal stability is another critical property and is measured using thernogravimetric analysis (TGA) in a dynamic mode. Values from this test are reported as the temperature at which the test specimen lost five percent of its initial weight.

Formulations

|  | Hand Cast |
|---|---|
| Nova 1994 PS resin | 40 g |
| Methylene chloride | 178 g |
| Flame Retardant | 0.2 g-10 g |
| Pentane | 4 g |

Experimental 1,1'-(1,2-dibromo-1,2-ethanediyl)bis-tribromobenzene

Step 1: General Procedure for Aromatic Bromination of Diphenylethane (DPE):

A 500 mL round-bottom, 4-neck flask equipped masterflex pump, mechanical stirrer, thermocouple, siltherm condenser, and HBr scrubber was charged with DPE (50 g, 0.274 mol), 100 mL of halocarbon solvent (dibromomethane (DBM), dichloroethane (EDC), or bromochloromethane (BCM)). The mixture was stirred to dissolve the DPE and $FeBr_3$ or Fe (0.0075 mole) was added. Bromine (5.5 equivalents) was added dropwise over two hours. The temperature of the reaction increased via exotherm from 22.degree. C. to 35.degree. C. HBr evolution was measured to gage the reaction. After the reaction, additional solvent was added to the reaction (enough to make up a 1 gram/3 mL product/solvent ratio) and 100 mL of deionized (DI) water or 5% HBr was added. The reaction was stirred until it turned light orange. The layers were then phase separated. Approximately 10% (by weight) of the product was removed and dried under vacuum using a rotary evaporator (rotovap). The dried sample was analyzed for total organic bromide and iron content.

|  | Theoretical |
|---|---|
| Formula Weight | 616.3 g/mol |
| Molecular Formula | $C_{14}H_{8.5}Br_{5.5}$ |
| Organic Bromide | 71.3 |
| Fe (by ICP) | <20 ppm |

1,1'-(1,2-dibromo-1,2-ethanediyl)bis-tribromobenzene

Step 2: Photolytic Procedure for Aliphatic Bromination of BromoDPE:

A 1 L round-bottom, 4-neck flask equipped with a 250 mL addition funnel, mechanical stirrer, thermocouple, siltherm condenser, and HBr scrubber was charged with multibrominated DPE (152.2 g; 0.245 mol) and 456 mL of halocarbon solvent (DBM, EDC, or BCM). The reaction mixture was heated to reflux. Either a GE 250 watt reflector lamp or Hanovia UV blacklights were used to catalyze the aliphatic bromination. Bromine (2 molar equivalents) was added dropwise over two hours. If solids were present at the beginning of the reaction, they dissolved after about 10% of the bromine was added. If using EDC or BCM, some solids may precipitate during the last 10% of the bromine addition. Stirring of the reaction was continued for 3-4 hours after the bromine addition and was monitored by HBr evolution. The reaction mixture was either rotovapped or solvent evaporated and filtered to isolate the product. Yield of the reaction was 50-95% depending on the method of isolation.

1,1'-(1,2-dibromo-1,2-ethanediyl)bis-tribromobenzene

Step 2: AIBN Procedure for Aliphatic Bromination of BromoDPE:

A 1 L round-bottom, 4-neck flask equipped with a mechanical stirrer, thermocouple, and a siltherm condenser was charged with multibrominated DPE (50 g; 0.81 mole) and 40 mL of halocarbon solvent (DBM, EDC, or BCM), bromine (28.5 g; 0.18 mol), and 40 mL of DI water. The reaction mixture was heated to 70° C. A slurry of 1.1 g AIBN and 5 mL of water was added over three hours. The reaction was stirred at 70.degree. C. for two additional hours after the last AIBN charge. The reaction mixture was then cooled and the aqueous layer was phase separated. The reaction mixture was washed with DI water and $NaHSO_3$ to remove any residual bromine, then DI water. The solvent was removed by rotovap or filtered to isolate the product. Yield of the reaction ranged from 62-95%.

The target analysis of the final product is:

|  | Theoretical |
| --- | --- |
| Formula Weight | 774.1 g/mol |
| Molecular Formula | $C_{14}H_{6.5}Br_{7.5}$ |
| Organic Bromide | 71.3 |
| Hydrolizable Bromide | >15% |
| Target Aromatic Bromine | 5.5-6 |
| Target Aliphatic Bromine | 1.5-2.0 |
| Average Aromatic Bromine | 6.0 |
| Average Aliphatic Bromine | 1.6 |
| Inorganic Bromide | <1% |
| TGA (5% weight loss) | >210° C. |
| Isothermal TGA (200° C./30 min) | ~88% |

In view of the many changes and modifications that can be made without departing from principles underlying the invention, reference should be made to the appended claims for an understanding of the scope of the protection to be afforded the invention.

What is claimed is:

1. A method for flame-retarding styrenic resins and foamed styrenic resins comprising incorporating an effective amount of at least one flame retardant compound comprising both aliphatic and aromatic bromine and has a 5% weight loss based on TGA analysis at between about 218° C. and 263° C., wherein the at least one flame retardant compound comprises a compound selected from the group consisting of

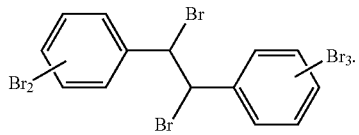

2. The method for flame-retarding styrenic resins and foamed styrenic resins according to claim 1 wherein the at least one flame retardant compound also comprises at least one additional flame retardant compound comprising both aliphatic and aromatic bromine and has a 5% weight loss based on TGA analysis at between about 218° C. and 263° C.

3. The method for flame-retarding styrenic resins and foamed styrenic resins according to claim 2 wherein at least one of the additional flame retardant compound comprises a compound selected from the group consisting of 1,1'-(1,2-dibromo-1,2-ethanediyl)bis-tribromobenzene, bis-(1-bromoethyl)bromobenzene, bis-(1-bromoethyl)dibromobenzene, bis-(1-bromoethyl)tribromobenzene, bis-(1-bromoethyl)tetrabromobenzene, 9,10-dibromo-9,10-dihydro octabromoanthracene, 9,10-dibromo-9,10-dihydro septabromoanthracene, 9,10-dibromo-9,10-dihydro hexabromoanthracene, 9,10-dibromo-9,10-dihydro pentabromoanthracene, 4-bromomethyl tetrabromobenzyl 2,4,6-tribromophenyl ether, and 4-bromomethyl benzyl 2,4,6-tribromophenyl ether.

4. The method for flame-retarding styrenic resins and foamed styrenic resins according to claim 3 wherein at least one of the additional flame retardant compound comprises 1,1'-(1,2-dibromo-1,2-ethanediyl)bis-tribromobenzene prepared in such a away that there are eight major components and several minor components that average to an aromatic bromine content of 5.5-6 bromine atoms and an average amount of 1.7-1.9 aliphatic bromine atoms.

5. An article of manufacture comprising a styrenic resin composition or foamed styrenic resin composition wherein said composition comprises an effective amount of at least one flame retardant compound comprising both aliphatic and aromatic bromine and has a 5% weight loss based on TGA analysis at between about 218° C. and 263° C., wherein the at least one flame retardant compound comprises a compound selected from the group consisting of

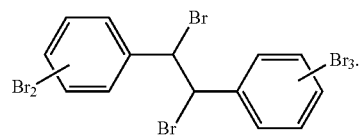

6. The article of manufacture comprising a styrenic resin composition or foamed styrenic resin composition according to claim 5 wherein the at least one flame retardant compound also comprises at least one additional flame retardant compound comprising both aliphatic and aromatic bromine and has a 5% weight loss based on TGA analysis at between about 218° C. and 263° C.

7. The article of manufacture comprising a styrenic resin composition or foamed styrenic resin composition according to claim 6 wherein at least one of the additional flame retardant compound comprises a compound selected from the group consisting of 1,1'-(1,2-dibromo-1,2-ethanediyl)bis-tribromobenzene, bis-(1-bromoethyl)bromobenzene, bis-(1-bromoethyl)dibromobenzene, bis-(1-bromoethyl)tribromobenzene, bis-(1-bromoethyl)tetrabromobenzene, 9,10-dibromo-9,10-dihydro octabromoanthracene, 9,10-dibromo-9,10-dihydro septabromoanthracene, 9,10-dibromo-9,10-dihydro hexabromoanthracene, 9,10-dibromo-9,10-dihydro pentabromoanthracene, 4-bromomethyl tetrabromobenzyl 2,4,6-tribromophenyl ether, and 4-bromomethyl benzyl 2,4,6-tribromophenyl ether.

8. The article of manufacture comprising a styrenic resin composition or foamed styrenic resin composition according to claim 7 wherein at least one of the additional flame retardant compound comprises 1,1'-(1,2-dibromo-1,2-ethanediyl)bis-tribromobenzene prepared in such a away that there are eight major components and several minor components that average to an aromatic bromine content of 5.5-6 bromine atoms and an average amount of 1.7-1.9 aliphatic bromine atoms.

* * * * *